US009354236B2

(12) United States Patent
Albar Ramirez et al.

(10) Patent No.: US 9,354,236 B2
(45) Date of Patent: May 31, 2016

(54) METHOD FOR IDENTIFYING PEPTIDES AND PROTEINS FROM MASS SPECTROMETRY DATA

(75) Inventors: Juan Pablo Albar Ramirez, Madrid (ES); Antonio Ramos Fernandez, Madrid (ES)

(73) Assignee: CONSEJO SUPERIOR DE INVESTIGACIONES CIENTIFICAS, Madrid (ES)

( * ) Notice: Subject to any disclaimer, the term of this patent is extended or adjusted under 35 U.S.C. 154(b) by 460 days.

(21) Appl. No.: 13/381,438

(22) PCT Filed: Jun. 30, 2010

(86) PCT No.: PCT/ES2010/070445
§ 371 (c)(1),
(2), (4) Date: Feb. 2, 2012

(87) PCT Pub. No.: WO2011/000991
PCT Pub. Date: Jan. 6, 2011

(65) Prior Publication Data
US 2012/0191685 A1     Jul. 26, 2012

(30) Foreign Application Priority Data
Jul. 1, 2009   (ES) .................................. 200930402

(51) Int. Cl.
| G06F 17/00 | (2006.01) |
| G01N 33/68 | (2006.01) |
| G06F 19/18 | (2011.01) |
| G06F 19/24 | (2011.01) |

(52) U.S. Cl.
CPC ............ *G01N 33/6848* (2013.01); *G06F 19/18* (2013.01); *G06F 19/24* (2013.01)

(58) Field of Classification Search
CPC ...... G01N 33/6848; G06F 19/18; G06F 19/24
USPC ......................................................... 707/706
See application file for complete search history.

(56) References Cited

PUBLICATIONS

Rohrbough, JG, Brescia, L., Merchant, N., Miller, S., Haynes, PA 2006. "Verification of single-peptide protein identifications by the application of complementary database search programs". J. Biomol. Tech 5, 327-332.
Higgs, RE, Knierman, MD, Freeman AB, Gelbert, LM, PatH, ST, Hale, JE 2007. "Estimating the Statistical Significance of Peptide Identifications from shotgun proteomics experiments." J. Proteome Res 6, 1758-1767.

(Continued)

*Primary Examiner* — Mariela Reyes
*Assistant Examiner* — Mohsen Almani
(74) *Attorney, Agent, or Firm* — Gerald E. Hespos; Michael J. Porco; Matthew T. Hespos (57) ABSTRACT

The present invention relates to a method of identifying peptides and proteins from mass spectrometry data using multiple search engines, wherein: a) the scores calculated on each engine are modeled; b) the presence of matching parameters is included, c) the distribution of meta-scores using distribution functions is modeled, d) scores of peptide and precursor protein are built. Among the main advantages of the invention it is worth mentioning its flexibility to be applied to an arbitrary number of engines, the use of matching parameters that add additional information not available with a single engine, the increase in the number of peptides-proteins identified or its versatility to incorporate other additional sources of information, depending on the type of experiment being examined.

17 Claims, 1 Drawing Sheet

(56) References Cited

PUBLICATIONS

Alves, G., Wu, WW, Wang, G., Shen, R.-F., Yu, Y.-K. (2008). "Enhancing confidence peptide identification by combining search methods". J. Proteome Res 8, 3102-3113.

Yu W., Taylor JA, Davis MT, Bonilla LE, Lee KA, Auger PL, Farnsworth CC, Welcher AA, Patternson SO (2010) "Maximizing the sensivity and reliability of peptide identification in large-scale proteomic experiments by Harnessing multiple search engines." Proteomics 10,1172-1189.

Karian ZA, Dudewicz, EJ (2000) "Fitting statistical distributions: the Generalized Lambda Distribution and Generalized Bootstrap Methods." Chapman and Hall/CRC. Transmitted Electronically in Three (3) Parts.

Arg Max; Wikipedia, the free encyclopedia, accessed at "https://en.wikipedia.org/wiki/Arg_max"; pp. 3; Jul. 23, 2015.

Arg Max; Wolfram Language Documentation, accessed at "https://reference.wolfram.com/language/ref/ArgMax.html"; pp. 3; introduced 2004, updated 2014.

Arg min and arg max; planetmath.org, accessed at "http://planetmath.org/argminandargmax"; 1 page; Jul. 8, 2004.

METHOD FOR IDENTIFYING PEPTIDES AND PROTEINS FROM MASS SPECTROMETRY DATA

FIELD OF THE INVENTION

The present invention falls within the field of methods for identification and structural characterization of proteins on a large scale through mass spectrometry techniques.

BACKGROUND OF THE INVENTION

Proteomics is one of the sciences of the post genomic era that has a greater impact on modern biotechnology, since it comprises the identification and quantification of large amounts of protein in extremely complex matrices (biological fluids, tissues or cell cultures, among others). Currently, the most successful and academically and industrially relevant techniques used in proteomics are those based on tandem mass spectrometry (MS/MS), which consists of the extraction of proteins from the sample to be tested, the digestion of these proteins with enzymes or other chemicals to obtain peptides (easier to analyze), the separation of these peptides, usually done by chromatographic techniques and placing them in a mass spectrometer in ionized form to measure their mass and fragmenting them within the mass spectrometer in order to obtain structural information so as to permit the identification of proteins formed by the analyzed peptides.

Current research in Proteomics based on tandem mass spectrometry involves the generation of large volumes of data typically containing thousands to millions of mass spectra. These spectra are allocated to sequences of peptides recorded in databases, using software called search engines. In the historical development of proteomics based on MS/MS, given the high number of spectra involved in the analysis, manual validation of spectrum-peptide correspondence has become impracticable in a short time, so it has become necessary to develop automatic procedures, not handled by the user, to identify the analyzed peptides, and discard spurious matches (known as false positives or false detections). These procedures include the use of algorithms based on statistical scoring systems to classify each spectrum analyzed in a sample, so that the higher the score, the greater the probability that the spectrum-peptide assignment is correct.

Currently, the existing differences among the various search engines on the market are derived from the pre-processing and standardization of MS/MS spectrum analyzed, as a result of the use of various statistical models and numerical methods in the scoring system for each engine. These differences pose a major problem when analyzing MS/MS spectrum using multiple search engines, as some sequences of peptides identified correctly in one of the engines may not be in others. This is a widely known fact by experienced spectrometers. The present invention comprises a method of combined search using multiple engines (hereinafter defined as meta-search) aimed at solving this problem, as well as optimization techniques for analyzing the spectra obtained by MS/MS. This method also provides a general criterion score (which we define as a goal-scoring) of the results obtained by different database engines using a sufficiently robust statistical modeling leading to a unique peptide spectrum allocation.

Despite the potential benefits that a meta-search method with multiple engines has, few attempts have been made in this direction so far. Among the most relevant ones, it is worth mentioning the work developed by Rohrbough et al. [1], Higgs et al. [2], Searle et al. [3] and Alves et al. [4]. On the other hand, within the state of the art related to research in proteomics, it is more abundant the existence of commercial products with comparative search options (which differs from the concept of meta-search) using several engines that present some software applications found in the market, such as the option "InChorus" by PEAKS search engine (distributed by Bioinformatics Solutions Inc.), the Rosetta Elucidator data analysis system (distributed by Rosetta Biosoftware), the Proteome Discoverer platform analysis (distributed by Thermo Fisher Scientific Inc.) or the Phenyx engine, distributed by Geneva Bioinformatics SA.

Another application of this technical field is the embodiment of the search methods in analytical devices of peptides and proteins that combine both hardware and software, and are marketed independently as "plug-and-play" workstations or servers that can be used simultaneously by multiple users. An example of such devices would be the Sorcerer 2 workstation, sold by Sage-N Research, Inc., or the configurable server distributed jointly by IBM and Thermo Electron Corporation. These devices do not integrate, to date, the simultaneous use of several engines through a meta-search method.

While the present invention shares some approaches and objectives with each of the aforementioned techniques, it is the only one of all methods that presents the following set of advantages:

The method for meta-search and meta-scoring system adds additional information that can not be obtained by searching with only one engine.

It uses a robust statistical modeling that allows the selection of a unique combination of peptide sequence, electric charge and chemical composition by spectrum (as opposed to the methods used by PEAKS, Rosetta Elucidator, Proteome Discoverer and Phenyx, which only use the results of multiple engines for comparative purposes, without the possibility of using a common statistical and a common meta-scoring system).

This method can be completely generalized for the use of any number of search engines (as opposed to the methods proposed in References [1] and [2], whose generalization to more than two engines is not feasible).

It uses a standard method that applies to the results of any search engine to obtain the statistical distribution functions, unlike the method described in Reference [3] and its commercial embodiment in the Scaffold application (distributed by Proteome Software Inc.) whose extension to more than the three studied engines would require a satisfactory distribution for each new search engine used.

It integrates, in its formulation, the use of matching parameters, defined as the number of other search engines that have supplied the same peptide candidate than a given engine. The use of matching parameters is not covered in the method contemplated in Reference [4], missing because of its absence a valuable part of the information, which contributes significantly to the increase in the number of identified peptides.

It automatically optimizes the values of all parameters involved in the process through statistical modeling, without the need to define any type of filter, arbitrary scoring mechanism or presetting values for the coefficients of the latter, unlike methods based on arbitrary multiple filters or predefined scoring mechanisms described in references [4] and [5].

As for protein detection, it uses a rigorous statistical method, unbiased, which uses a filtering defined by the error rates in the peptide-sequence allocations.

Additionally, the claimed method is flexible enough to incorporate other sources of additional information to the consistency of the engine, such as the filtering through the mass error of the sequence precursor ion (defined as the difference between the theoretical mass of an ion peptide and the measuring of the mass obtained by the spectrometer, using either its molecular mass or its mass/charge ratio, m/Z), the error in the retention time (defined as the characteristic retaining time during chromatographic separation), the prediction error of the isoelectric point (similar to the previous factor, when the peptides are fractioned using isoelectric focusing separation techniques), ionic mobility (in the mass spectrometer incorporating such an analysis, based on ion accumulation of chemical species under the action of an electric field), the specificity of the enzymatic digestion used (ie, the characteristics of protein segmentation depending on the type of enzymes used for digestion), the detection of multiple isotopic patterns for a same peptide (common in stable isotopic labelling experiments used in quantitative proteomics applications) or consistent with the sequence obtained by MS/MS without using a search engine (known as de novo sequencing of the information.) This flexibility makes it possible for the meta-search method to integrate data using different sample preparations, different methods of protein digestion and different mechanisms of ion fragmentation, which makes it a suitable tool for large-scale identification of proteins.

The present invention is based on a meta-search method using the results of spectrum-peptide allocation obtained in different search engines on hybrid target/decoy databases containing a 1:1 ratio of real proteins against false proteins. These false proteins are usually obtained reversing the sequence of each of the real proteins. As a preliminary step to the allocation of meta-results, the method of analysis of results in each of the engines studied separately is performed using the technique developed by Ramos-Fernández et al [6] (developed for using a single search engine) based on the use of generalized Lambda distributions (GLD's). Said GLD's are functions of four extremely flexible parameters that can represent with great precision the majority of the most important families of continuous probability distributions used in statistical modeling of histograms. The GLD's model (described in, for example, the work of Karian et al [6]) has not been previously used to perform combined searches on multiple engines of sequence databases, and provides the theoretical framework of the statistical model on which the meta-search method and meta-scoring here claimed operates. Unlike the model of reference [7], the invention claimed here is presented as a method that can be implemented automatically, providing objective criteria that will allow the election of the GLD that best fits the observed results without the need of personally supervising each of the candidate models.

REFERENCES

[1] Rohrbough, J G, Brescia, L., Merchant, N., Miller, S., Haynes, P A 2006. "Verification of single-peptide protein identifications by the application of complementary database search programs". J. Biomol. Tech 5, 327-332.
[2] Higgs, R E, Knierman, M D, Freeman A B, Gelbert, L M, Patil, S T, Hale, J E 2007. "Estimating the Statistical Significance of Peptide Identifications from shotgun proteomics experiments." J. Proteome Res 6, 1758-1767.
[3] B C Searle, M. Turner, A. Nesvizhskii (2008). "Improving sensitivity by Combining results from multiple MS/MS Search Methodologies." J. Proteome Res 7, 245-253.
[4] Alves, G., Wu, W W, Wang, G., Shen, R.-F., Yu, Y.-K. (2008). "Enhancing confidence peptide identification by combining search methods". J. Proteome Res 8, 3102-3113.
[5] Yu W., Taylor J A, Davis M T, Bonilla L E, Lee K A, Auger P L, Farnsworth C C, Welcher A A, Patternson S D (2010) "Maximizing the sensitivity and reliability of peptide identification in large-scale proteomic experiments by Harnessing multiple search engines." Proteomics 10, 1172-1189.
[6] Ramos-Fernandez, A. Paradela, A., Navajas, R., Albar, J P 2008. "Generalized method for probability-based peptide and protein identification from tandem mass spectrometry data and sequence database searching." Mol. Cell. Proteomics 7, 1748-1754.
[7] Karian Z A, Dudewicz, E J (2000) "Fitting statistical distributions: the Generalized Lambda Distribution and Generalized Bootstrap Methods." Chapman and Hall/CRC.

SUMMARY OF THE INVENTION

An object of this invention is to provide a general method for identifying peptides and proteins using data from tandem mass spectrometry.

Another object of this invention is to provide a meta-search engine in which the candidate peptides are obtained from multiple search engines in sequence databases.

These and other objects are achieved by a method in which:

A search using at least two search engines in sequence databases (meta-search) is used and can be extended to the analysis of any number of engines. This generates additional information that cannot be gained through the search with a single engine.

Candidate peptides are classified in each search engine to build a model of generalized Lambda distribution (GLD's). A theoretical support completely general, applicable to an arbitrary number of search engines is achieved in this way.

Data from multiple search engines is integrated through a meta-scoring system based on generalized probability distributions and generalized p-values (the latter defined as the values of probability that specific peptide sequence detection has been produced randomly). A robust statistical modeling that allows the selection of a unique combination of peptide sequence, electric charge and chemical composition by spectrum is achieved this way.

The meta-scoring system includes the presence of matching parameters that provide information about the coincidence of peptide-sequence allocation in multiple engines. Greater analysis information is achieved, which contributes significantly to the increase in the number of peptides identified.

In a preferred embodiment of the present invention, the integration of data from multiple search engines is carried out through a system of meta-scoring based on generalized Lambda distributions (GLD's) and generalized p-values. A unique distribution of meta-scores is achieved as well as a classification system of peptide sequence allocation that integrates data from all search engines used, providing additional information that is not available through the use of a single engine.

In a preferred embodiment of the present invention a generalized error rate is estimated, either through false discovery rate (usually appointed by the English term, "false discovery rate", or FDR, and defined in the detailed description of invention) through the decoy hit rate (designated by the English term "decoy hit rate" or DHR, and defined in the detailed description of the invention), through the probability of obtaining at least one false positive (called "Familywise error rate", FWER, and defined in the detailed description of the invention) or through any other statistical measure of error in identification. This way, an estimate of accuracy in the peptide sequence allocations for a given data set is facilitated.

In a preferred embodiment of the present invention, p-values corresponding to the allocation of precursor proteins in data sets are calculated, as well as error rates FDR and DHR of said proteins. This way, a single set of data about the added information from all search engines on the precursor protein of the detected peptides is achieved.

In a preferred embodiment of the present invention, a different weight coefficient is assigned to each engine during the meta-scoring phase, being this set a priori or calculated depending on factors such as, the tendency to match of some of the selected engines (using, for example, similar algorithms that produce an overlap), that any of the engines had a much higher yield than the rest, or any other situation in which you want to perform an asymmetric weighting among the various sources employed. This incorporates the possibility of promoting the value of information obtained by some engine on others.

In a preferred embodiment of the present invention, a relationship is established between the meta-score calculated for a spectrum-peptide allocation and the characteristics of the sequence of the peptide candidate, such as length, presence or absence of sub-sequences or structural motifs as well as the matching of the sequence of the peptide with what is expected from the cutting mechanism of the chemical agent used in the digestion of proteins. This allows to incorporate the factors expected in the obtained sequences to the meta-scoring method, depending on the features of the experiment analyzed, in order to improve the discrimination between correct and incorrect allocations.

In a preferred embodiment of the present invention, the meta-search method is integrated on a device designed to analyze results of tandem mass spectrometry, comprising electromagnetic, electronic or computer made in the form of hardware and/or software mechanical means, being aimed to form a data analysis system for the identification of peptides and proteins.

Other features and advantages of the present invention will be understood from the following detailed description and an illustrative embodiment of its object in relation to the accompanying figure.

DESCRIPTION OF THE FIGURES

FIG. 1 is a schematic diagram of the meta-search method described herein. It represents the search of MS/MS sequences on spectra sets 1 through the use of multiple search engines M available in the market on hybrid target/decoy databases 2. Scores x associated with the decoy results are sorted by the state of the charge of the precursor ion and are represented as probability densities y, in conformity to a GLD model and calculating their p values V. P-values V obtained are plotted against their relative frequency x'. It also includes the GLD model used to represent the distribution of the meta-scores x" as densities of probability y, performed during the calculation of meta-score phase 3 described by the present invention.

DETAILED DESCRIPTION OF THE INVENTION

The meta-search method claimed in the present invention comprises the following steps:
1. MS/MS Search: The search in the MS/MS databases is performed through the search engines used in the meta-search process. The list of peaks of the spectra is used as input of the system, determining the parameters of each search engine according to a common scheme, fixing the precursor mass tolerance and the fragment ion mass tolerance (ie, errors tolerated in the calculated mass values), the specificity of enzymatic digestion (ie, the type of fragmentation produced by the enzyme used to digest proteins), or any other parameters depending on the engine used and the data set analyzed.

2. GLD Settings: a model based on generalized Lambda distributions (GLD's) is used to model score distributions of spectrum-peptide matches. The generalized Lambda function may be defined by its percentile distribution:

$$Q(y) = Q(y, \lambda_1; \lambda_2; \lambda_3; \lambda_4) = \lambda_1 + \frac{y^{\lambda_3} - (1-y)^{\lambda_4}}{\lambda_2}, \quad (1)$$

where $0 \leq y \leq 1$. Parameters $\lambda_1$ and $\lambda_2$ are, respectively, the location parameter (defined as the displacement of distribution in the x-axis) and scale parameter (which determines the height of the distribution) and $\lambda_3$ and $\lambda_4$ determine, respectively, the asymmetry of the distribution (with respect to a vertical axis) and its kurtosis (defined as the degree of concentration around the peak). An adequate description of the necessary restrictions on these parameters to provide valid GLD's can be found, for example, in Reference [7]. From the percentile function, the probability density in $x=Q(y)$ is obtained as $$f(x) = \frac{\lambda_2}{\lambda_3 y^{\lambda_3} + \lambda_4 (1-y)^{\lambda_4 - 1}}. \quad (2)$$

Since y is defined as the probability that $x \leq Q(y)$, the modeling of the GLD's from the histograms of observed data requires the conversion of data points at a frequency of relative scale, the calculation of the value of Q (y) for all points and the clustering of data points according to said value. In order to adjust the GLD's to the data histograms, the percentile method described in Reference [7] is used, in which four statistic samples used as estimates of the parameters of the distribution are calculated. Of all the sets of parameters ($\lambda_1$, $\lambda_2$, $\lambda_3$, $\lambda_4$) compatible with the sets of estimates obtained for each histogram, the GLD that best fits the data observed is selected, like for example the one that minimizes the error indicator referred to, as defined by the expression $$\sum_{i=1}^{K} (y_i - f_i)^2, \quad (3)$$

where $y_i$ is the observed value in the i-nth box of the score histogram (with K boxes) and $f_i$ is the value predicted by the GLD model in consideration (probability density), in a similar way to a least squares adjustment.

3. Estimating p-values and error rates in the identification of peptides: As there is no closed-form expression for the probability function $y=F(x)$, all p-values associated with each data point is calculated numerically. Given a set of p-values associated with the peptides and sorted in ascending order, the expected proportion of data observations that exceed a threshold p-value $p_i$ depends on the volume of data, as well as the number i of points that have equal or greater value-p. This amount, known as the false detection rate (FDR), gives a measure of the expected error:

$$FDR_i = \frac{Np_i}{i}. \quad (4)$$

Error rates can also be estimated by searching hybrid target/decoy sequence databases, counting the number of decoy hits that exceed a certain threshold of value-p. This value, calculated from the proportion of decoy identifications observed among all identifications done for a given filter, is called decoy hit rate (DHR) and is defined as $$DHR_i = \frac{\alpha D_i}{i}, \quad (5)$$

where $D_i$ is the number of allocations to decoy peptide with a p-value less than or equal to $p_i$. Parameter $\alpha$ varies depending on the type of sequence database used. For hybrid target/decoy databases with inverted sequence, $\alpha$ is equal to 2.

Other embodiments of the present invention may include the use of other measures of error estimation, for example, the probability provided by the "Familywise error rate" (FWER), defined as $$FWER_i = 1 - (1-p_i)^N, \quad (6)$$

where $p_i$ is the $i^{th}$ best p-value from N p-values obtained.

4. Calculating p-values and protein identification scores and error rates: The peptide sequence allocations are grouped within a precursor protein sequence. For p-values of a given number h of ion candidates, assigned to a given protein, the value of the protein score is defined as $$S_p = \sum_{i=1}^{h} -\log(p_i), \quad (7)$$

where $p_i$ are the p-values of the candidate ions calculated in the corresponding GLD models. Optionally, the value of the protein score can also be defined as the sum of the peptide meta-scores. In the same way, the values of FDR and DHR are calculated as described in the previous section for each group of similarity (this term defined as the set of proteins that share at least one identified peptide), taking as a p-value the smaller protein p-value within the group.

Figure 1:
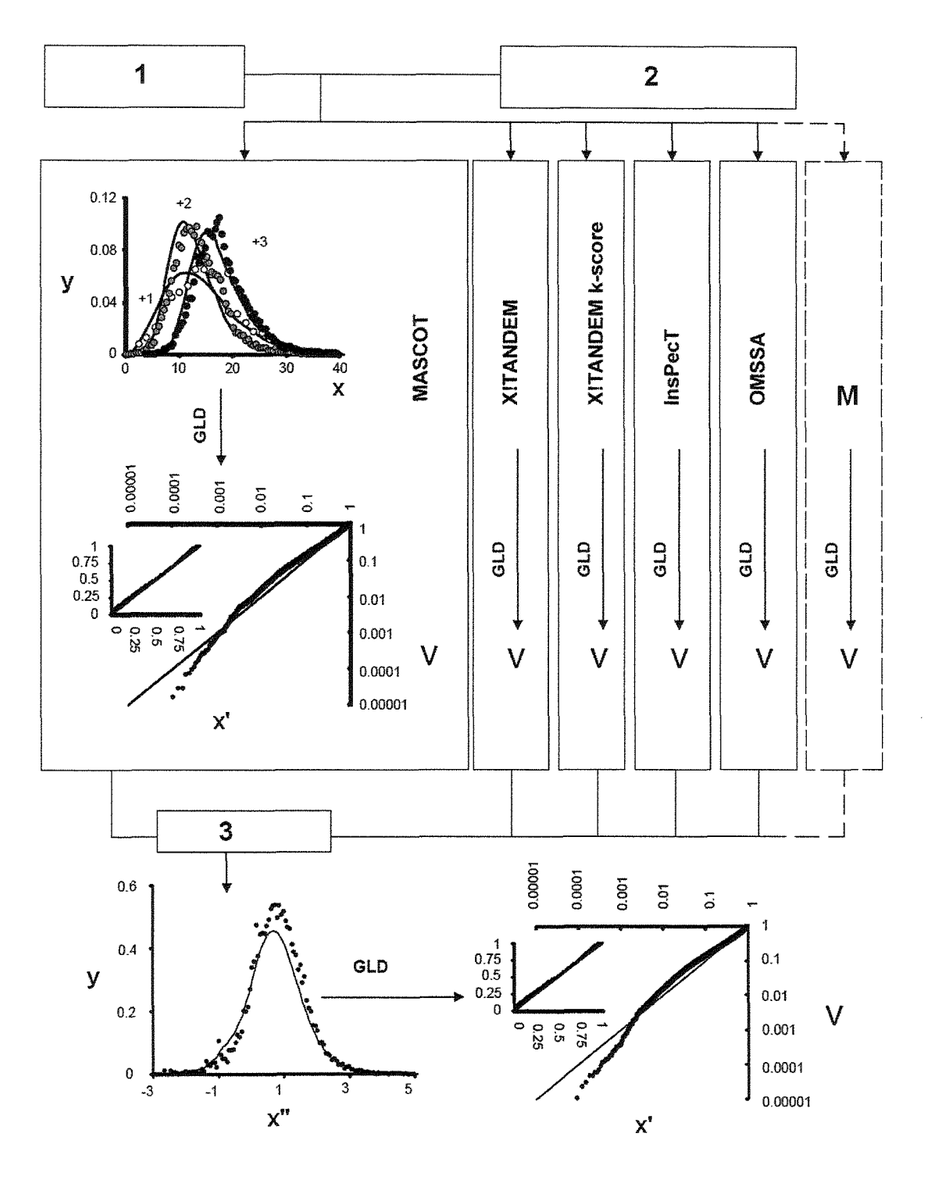

5. Integration of data from multiple search engines and meta-score calculation: The strategy of integrating data from multiple search engines is represented schematically in FIG. 1. The MS/MS spectra are assigned to peptide sequences using multiple sequence search engines (meta-search). Current examples of these engines are, for example, MASCOT applications (available from Matrix Science Inc.), X! TANDEM (distributed by The Global Proteome Machine Organization and Labkey) OMSSA (distributed by the National Center for Biotechnology Information), Phenyx (distributed by Geneva Bioinformatics) and InsPect (Distributed by the Center for Computational Mass Spectrometry), among others. After the allocation of sequences in the candidate peptides, GLD's are adjusted and all p-values are calculated with their corresponding scores, as described in the previous paragraphs. In a preferred embodiment of the present invention a table containing the maximum score for each search engine for each MS/MS spectrum in the dataset is constructed. With this information, the meta-score of a spectrum j given a set of data is defined as $$S_j = \underset{k}{\operatorname{argmax}}(GLD(1-p_{jk}, 0, 0.2142, 0.1488, 0.1488) + \beta A_{jk}), \quad (8)$$

where the value of k that maximizes the value of the score $S_j$ for a given spectrum is taken. The variable $p_{jk}$ is the p-value calculated by the GLD model for a given k search engine associated with a candidate peptide. The distribution function $GLD(1-p_{jk},0,0.2142,0.1488,0.1488)$ is the percentile function value (defined as the inverse function of the cumulative distribution) of the GLD in the $p_{jk}$ p-value, so as to obtain approximately a normal distribution, provided p-values are evenly distributed. $A_{jk}$, defined as the matching parameter of the search engine, indicates the number of other search engines that have provided the same candidate peptide that the $k^{th}$ engine, for the $j^{th}$ spectrum. Finally, $\beta$ is a coefficient whose value is to be optimized specifically for each data set, selecting that value that maximizes the number of spectra recovered for a given value of the DHR. The optimal value of the matching coefficient can also be estimated using a different numerical method, using a more complex formulation for reclaiming the correlation between engines, rather than assuming a linear dependence between the number of the matching and the magnitude of the bonus.

In a second preferred embodiment of the invention a procedure is carried out by which, for a given spectrum j, instead of taking the best candidate for each engine, the I best candidates are taken, sorted from highest to lowest score (i=1, . . . , I). Subsequently we define an extended matching parameter $A_{ijk}$, which designates the number of other engines (k=1, . . . , K) that provide as a better candidate (i=1) the same peptide that the $i^{th}$ candidate of the $k^{th}$ engine. In addition, a number of accessory parameters $x_1, \ldots x_n$, representing the contribution of n additional sources of information, these sources of information comprising one or more of the following:

a) Sources of information related to the physiochemical characteristics of the candidate peptide sequences:

Error of the value m/z of the precursor ion: absolute error in measuring the mass/charge ratio of the precursor ion of the fragmentation spectrum in consideration, in absolute value, given a candidate peptide sequence. The calculation of the expected value of the precursor ion mass/charge ratio is trivial from the candidate peptide sequence and the estimated charge of the precursor ion.

Retention time error: absolute error of the retention time of fragmentation spectrum in consideration, in absolute value. It is applied when the data have been obtained using reverse phase chromatography (RPC) coupled with mass spectrometry.

Error of the fragmentation retention time: absolute error of retention time (at the stage of peptide pre-fragmentation) of the fragmentation spectrum in consideration, in absolute value. It is applied when the data has been obtained by peptide fragmentation through any suitable biochemical method (ion exchange, reverse phase at basic pH, isoelectric focusing, etc. . . . ) prior to reverse phase chromatography coupled with mass spectrometry. The observed value for each spectrum may be the retention time at which each fraction was obtained, if a measure of this value is available, or simply the fraction number (which, in fact, is a transformation of order of the previous value).

b) Sources of information related to the expected behaviour of the chemical or enzyme that has generated the peptides analyzed by mass spectrometry:

Number of internal targets: Number of cutting sites of the enzyme or chemical agent containing the candidate peptide sequence. A binary variable for each value of number of internal targets observed in the experiment is defined, whose value is 1 if this number matches the number of targets inside the candidate peptide sequence, and 0 otherwise.

Number of specific extremes: Number of extremes of the candidate peptide sequence whose sequence is compatible with the expected behaviour of the chemical agent or enzyme that generated the peptides. A binary variable is defined for each value of number of specific extremes observed in the experiment, whose value is 1 if this number matches the number of targets inside the candidate peptide sequence, and 0 otherwise.

c) Sources of information related to the generation of multiple spectra from a single peptide:

Alternative forms-electric charge: Number of different electric charges with which (provided by the engine as a better candidate for a given spectrum) the candidate peptide in the experiment has been provided. The disparity of electric charges of a given peptide depends on the mechanism of ionization.

Alternative forms-isotopic signatures: Number of configurations of stable isotopic signatures with which (provided by the engine as a better candidate for a given spectrum) the candidate peptide sequence in the experiment has been detected, when the data come from stable isotope labelling experiments (stable isotope labelling, —SILE).

Alternative forms-chemical modifications: Number of forms of chemical modification with which (provided by the engine as a better candidate for a given spectrum) the candidate peptide sequence in the experiment has been detected, when the peptides may undergo chemical change during the process of analysis, whether such changes are induced by the user or not.

Alternative forms-fragmentation mechanisms: Number of fragmentation mechanisms of ions that have generated spectra through which (provided by the engine as a better candidate for a given spectrum) the candidate peptide sequence in the experiment has been detected, when the experiment combines data obtained using different fragmentation mechanisms (eg, collision-induced dissociation (CID) or electron transfer dissociation (ETD)).

d) Sources of information related to specific engine characteristics and performance depending on the type of data:

Precursor ion electric charge: a binary variable for each value of electric charge observed in the experiment is defined, whose value is 1 if the precursor ion electric charge is equal to said electric charge, and 0 otherwise. It is used to promote or penalize forms of electric charge for which the performance of a given engine is particularly good or bad.

Fragmentation mechanism: a binary variable is defined for each ion fragmentation mechanism used in the experiment, whose value is 1 if the spectrum in consideration has been obtained by said fragmentation mechanism, and 0 otherwise. It is used to promote or penalize fragmentation mechanisms for which the performance of a given engine is especially good or bad.

Delta score and additional scores: a generic delta score is defined for all engines as the score given by the engine to a candidate peptide sequence minus the highest score observed among the remaining candidates for the same spectrum with a lower score. This score is similar to additional differential scores usually called 'delta', which provide some engines such as SEQUEST. Additional score is defined as any amount that is capable of being used as scoring, and which is provided by the engine along with the main score, although it is usually much less informative than this. For example, medianPRMscore, totalPRMscore, fractionY and fractionB variables, provided by the engine Inspect can be defined as such variables, along with its main scoring, called MQscore.

e) Sources of information related to the precursor protein of the candidate peptides:

Precursor protein (complete experiment): Establishes a relationship between the number of peptides with which the precursor protein has been identified (from all spectrum of the experiment) of a given candidate peptide sequence and the length of the sequence of said protein. For this purpose proteins are first sorted from highest to lowest number of peptides identified, and secondly by decreasing protein length and then the relative ranking is used in both cases to generate, through a standardized normal inverse function, variables that follow a standard normal distribution. The difference between these two variables is taken as the protein score.

Precursor protein (fraction experiment): Same as above, but the number of peptides of the same protein among the spectra of a certain fraction of the experiment are counted, and not of the entire experiment. It can be used when a fractioning of proteins has been made, using any appropriate biochemical technique, prior to the generation of peptides to be analyzed by mass spectrometry.

Precursor protein (grouping): the number $k_t$ of different fractions in the experiment is counted, in which peptides of the precursor protein of the candidate peptide sequence in question appear. A large number K of random samples (eg. K=1000) of peptides identified in the experiment of size N, where N is the number of peptides identified from the precursor protein, are taken and the number $k_s$ of fractions different than those from the peptides of the sample are counted. The number of random samples R in which $k_s$ takes a value greater than $k_t$, is counted and the source of information for the grouping of the precursor protein is defined as R/K. It can be used when a fractioning of proteins has been made, using any appropriate biochemical technique, prior to the generation of the peptides to be analyzed by mass spectrometry.

It is possible, in addition, to use numerical transformations of additional sources of information mentioned before, whether they are transformations of order, non-linear transformations, arbitrary categories based on ranges of values, probabilities or probability densities calculated from these additional sources of information, replacing these or in combination with these, using these transformations also as additional sources of information.

After determining what sources of information are used, the extended score of the $i^{th}$ candidate provided for the $i^{th}$ spectrum for the $k^{th}$ engine is defined as $$s_{ijk} = GLD(1-p_{ijk}, 0, 0.2142, 0.1488) + \beta_1 x_{1ijk} + \ldots + \beta_n x_{nijk} + \gamma A_{ijk}), \quad (9)$$

where $p_{ijk}$ is calculated as described above for all candidates of each engine from the score provided by the engine, the coefficients $\beta_1, \ldots \beta_n$ and $\gamma$ are optimized by any mathematical optimization method in several dimensions, for example by maximizing the number of spectra or peptides recovered by setting a threshold of DHR. In each iteration of the optimization method the I best candidates for K engines are reordered from largest to smallest value of $s_{ijk}$ and index i are reassigned in order to recalculate the values $A_{ijk}$. Finally, we define the meta-score of the $j^{th}$ spectrum as:

$$S_j = \underset{i,k}{\mathrm{argmax}}(s_{ijk}) \quad (10)$$

where i, j and k are integers, taking the $i^{th}$ candidate of the $k^{th}$ engine, as the candidate peptide for the $i^{th}$ spectrum, such that the values of i and k maximize the value of $S_j$.

In a third preferred embodiment of the invention, the matching parameter is defined in its weighted form as follows:

$$A_{ijk} = \sum_{l=1, l \neq k}^{k} w_{kl} a_{ijkl}, \quad (11)$$

where a is the matrix of binary variables of size K×K that indicates which of the K engines provide the same peptide candidate that the $k^{th}$ engine, and w is a matrix with weight coefficients of matches among engines. It should be noted that setting to 1 all the values of the matrix w the meta-score equation 9 is obtained, and setting i=1 the meta-score equation 8 is also obtained. The value of these coefficients could be calculated, for example, from the matching frequencies among engines observed in the decoy peptides, or assuming the same initial value for all of them (eg. 1/(K(K−1))) and then optimizing these values as described for equation 9.

In a fourth preferred embodiment of the invention, a different weight coefficient is assigned to each engine during the meta-scoring, and this is set a priori or calculated, so that it is possible to incorporate the possibility of favouring the results obtained by some engines over others, if the particularities of the analyzed experiment would require it. The value of these coefficients could be calculated similarly to those described above.

In a fifth preferred embodiment of the invention, after generating meta-scores from each engine, an order of integration of additional sources of information is established, so that, for a given engine, a single additional source of information is incorporated to the meta-score, ignoring the matching information with other engines in equation 9, and its coefficient β is optimized using a numerical optimization method in only one dimension. After obtaining a new meta-scoring through this process, a new source of information is taken. This process is repeated until all the additional sources of information have been incorporated into the meta-score. The advantage of this process of meta-scoring incorporating additional sources of information in stages is that it has the necessary theoretical properties to eliminate any correlation among additional sources of information. After updating the meta-scoring of all engines, the matching information is incorporated, using the methods described in equations 8 or 9, and then the method described in Equation 10.

In a sixth preferred embodiment of the invention, an order of integration of the various search engines is established, so the process begins with two engines (preferably those two that provide the highest sensitivity, for example defined as the number of identifications a given error rate) and the equations 8 or 9 and equation 10 are applied. The result of this process is like a new engine 'consensus', then this result is taken together with the third engine and the equations 8 or 9 and equation 10 are applied. The process is repeated until all the engines have been incorporated into the 'consensus' preferably in descending order of their sensitivity. The advantage of this process of meta-scoring in stages is that it has the necessary theoretical properties to eliminate any correlation among engines.

After the candidate peptide sequences have been allocated to all MS/MS spectra, redundancy is eliminated, maintaining, for each combination of peptide sequence, electrical charge and chemical structure pattern, the one that has the highest meta-score. Subsequently, we obtain a unique distribution of meta-scores for each data set, as the meta-scores are independent from the precursor ion state of charge. From the p-values obtained as described in the above points, both the error rates FDR and DHR (at both levels, peptide and protein) as well as the p-values for proteins can be calculated.

Among the advantages of the meta-search method described by the present invention over other methods of known sequence searching, the following are included:

The method can be completely generalized to be applied to any number of search engines.

It uses a standard method to obtain statistical distribution functions, applicable to the results of any search engine.

It uses a robust statistical modeling that allows the selection of a unique combination of peptide sequence, electric charge and chemical composition pattern by spectrum.

The meta-search method and its meta-scoring system adds additional information that can not be obtained by searching with only one engine.

It integrates, in its formulation, the use of matching parameters, defined as the number of other search engines that have supplied the same peptide candidate than a given engine.

As for protein detection, it uses a rigorous statistical method, unbiased, which uses a FDR filtering.

Additionally, the claimed method allows incorporating other additional sources of information to the matching of the engine, such as the mass error of the precursor peptide, the error in the retention time, the specificity of enzymatic digestion or the matching with novo sequencing of the information. This flexibility allows the meta-search method the integration of data using different sample preparation, protein digestion methods and mechanisms of ion fragmentation.

By way of example, the results of tests conducted by the method claimed by the present invention are included here (see Table 1a-1f) and Table 2a-2d)), for samples of publicly available RaftFlow data (available on the internet repository SourceForge), PAe000038-39 (available on the website PeptideAtlas) PAe000114 (also in PeptideAtlas) iPRG2008 (the Association of Biomolecular Resource Facilities Proteome Informatics Research Group), evaluated for two sets of different search parameters (and distinguished by the names iPRG2008 and iPRG2008-NE). A detailed description of these data sets and related experiments can be found in Reference [6]. Also, the results at the peptide level of the following experiments carried out in the Proteomics Laboratory of the National Center of Biotechnology, National Research Council are included: Experiment SKHep-LA-I is based on the enrichment of peptides that are natural ligands of the molecules of the major histocompatibility complex type I (MHC-I). In this experiment the peptides are purified from cell line Sk-Hep, which express class I alleles HLA-A*0201, HLA-A*2402, HLA-B*3502 and HLA-B*4403. These peptides are generated by a natural process of digestion within the cell, bound to MHC molecules and transported to the cell surface, where they are presented to immune system cells. The different alleles of the genes that encode the MHC proteins may have a different repertoire of peptide ligands with slightly different structural properties. It is believed that some of these alleles are associated with autoimmune diseases, so having automated tools for large-scale characterization of repertoire of MHC molecules (either type I or II) is of considerable biomedical interest. The CID HLA-ETD experiment is a replica of the previous experiment, unlike spectra MS/MS were obtained using two different fragmentation mechanisms known by its initials in English as a CID (collision-induced dissociation) and ETD (electron transfer dissociation). The phosphopeptides experiment ABRF2010 corresponds to the analysis, also generating both CID and ETD spectra of phosphopeptides enriched by chromatography IMAC (Immobilized metal affinity chromatography), from a human protein sample provided by the Association of Biomolecular Research Facilities (ABRF). Phosphorylation is a post-translational modification of great importance in intracellular signaling processes, so that the results of identification of phosphopeptides by mass spectrometry shown here are of great importance in the field of biomedical research and both basic and applied biotechnology. The E coli SILE-SILAC experiment corresponds to the analysis of a sample from two populations of Escherichia coli bacteria labelled in culture with different isotopic forms of the aminoacid lysine (native or heavy form 13Cx6, 15Nx2, +8 Da) using the technique SILAC (Stable Isotopic Labelling by Amino acids in Cell Culture), whose protein extracts were fractionated by electrophoresis in polyacrylamide gel before digestion with trypsin. The experiment "Serum Frac. RP-basic pH" corresponds to the analysis of a sample of human serum which, after digestion with trypsin of the protein extract, obtained peptides were fractionated by reversed phase chromatography at basic pH (about 10.9).

The processing of data from different experiments has been performed using all four search engines InsPect, MASCOT, X! TANDEM (the latter used in two scoring versions, classical and "k-score") and OMSSA. The results obtained by the meta-search method claimed by this invention are summarized in Tables 1 and 2. For most data sets used, the combined meta-scoring system of all the search engines, using the p-values obtained by GLD modeling, provides a substantial increase in the number of peptides identified, compared with individual results obtained in any other engines in consideration. In the case of PAe000114 experiment, as it is clearly dominated by InsPect engine results, the results of the meta-search excluding said engine, are also included for comparison. The combination of the other engines, including matching information, provided a 19% higher efficiency than that obtained by OMSSA individually, and even greater efficiency in the rest of the engines. In general, the use of matching information improves the sensibility of all experiments, increasing between 9% to 26% the number of correctly identified peptides (with a FDR≤0.05 on a non-redundant set). Regarding the detection of proteins, the number of identifications with said error threshold increases between 6% and 60% after being sorted by meta-score. Table 2 (a-d) shows the results of the meta score process incorporating none, one or several sources of additional information in stages, as well as using data from a single engine or multiple engines in stages and using matching information. As it can be seen, all additional sources of information described help to increase the efficiency of the process of meta-scoring, judging by the significant increase in the number of allocations spectrum-sequence recovered to a certain error rate value, especially when using several of these additional sources of information in combination. Note that some of these additional sources of information are based on peculiarities related to experimental design that no search engine is able to incorporate into their scoring system, as deviations from the expected values of retention time, retention time during peptides fragmentation prior to analysis by mass spectrometry (Serum frac. experiment. basic pH), previous protein pre-fragmentation (SILE-SILAC experiment), alternative forms of charge, isotopic signatures (SILE-SILAC experiment) or mechanisms of fragmentation (CID experiments HLA-ETD and ABRF2010 phosphopeptides.), etc. Furthermore, the method described allows to optimally use and continue extracting information from these sources even in cases where the engine already uses these sources in its scoring system, as in MASCOT, which internally uses the error in the m/z value of the precursor ion to calculate their scores (see data for the experiment Serum frac. basic pH) as well as easily incorporate delta scores and supplementary scores provided by the engine in addition to the main score (see experiment ABRF2010 phosphopeptides, engine Inspect data and Serum frac experiment. pH basic, MASCOT engine data). Under these conditions, the effectiveness of the process is even greater when using information from multiple engines instead of a single engine, as clearly seen in experiments HLA-ETD and CID ABRF2010 phosphopeptides.

Tables of Results

Table 1 (below): Comparison between modeling results using a single engine for different experiments and the results using the meta search method. The indices used are: I, InsPect, K, X-TANDEM with "k-score"; M, MASCOT, OR, OMSSA, T, X! TANDEM classic. Comma-separated lists correspond to the use of multiple engines. "Concord." Indicates if the matching information has been taken into account. "No. Pept." Indicates the number of non-redundant peptide matches obtained for the FDR filter (or DHR, if any) given. "No. Prot" indicates the number of protein aggregation groups obtained for the FDR filter (or DHR, if any) given. "N/a" indicates "not applicable."

TABLE 1

| Engine (%) | Concord. | No. Pept. (FDR ≤ 0.05) | DHR | No. Pept. (DHR ≤ 0.05) | No. Prot (FDR ≤ 0.05) | Prot DHR | No. Prot (DHR ≤ 0.05) |
|---|---|---|---|---|---|---|---|
| a. RaftFlow Experiment ||||||||
| I | n/a | 1751 | 0.037 | 1851 | 410 | 0.062 | 360 |
| K | n/a | 1897 | 0.038 | 1986 | 455 | 0.048 | 456 |
| M | n/a | 1565 | 0.06 | 1511 | 411 | 0.044 | 422 |
| O | n/a | 1720 | 0.029 | 1825 | 447 | 0.072 | 430 |
| T | n/a | 1545 | 0.044 | 1579 | 426 | 0.069 | 412 |
| I, K. M, O, T | no | 2489 | 0.042 | 2552 | 527 | 0.059 | 515 |
| I, K, M, O, T | yes | 2708 | 0.049 | 2714 | 567 | 0.062 | 555 |
| b. PAe000038-39 Experiment ||||||||
| I | n/a | 522 | 0.042 | 572 | 150 | 0.053 | 108 |
| K | n/a | 455 | 0.105 | 58 | 91 | 0.042 | 96 |
| M | n/a | 521 | 0.054 | 505 | 130 | 0.046 | 145 |
| O | n/a | 616 | 0.058 | 579 | 182 | 0.062 | 154 |
| T | n/a | 409 | 0.058 | 394 | 149 | 0.067 | 147 |

TABLE 1-continued

| Engine (%) | Concord. | No. Pept. (FDR ≤ 0.05) | DHR | No. Pept. (DHR ≤ 0.05) | No. Prot (FDR ≤ 0.05) | Prot DHR | No. Prot (DHR ≤ 0.05) |
|---|---|---|---|---|---|---|---|
| I, K, M, O, T | no | 807 | 0.138 | 443 | 151 | 0.066 | 147 |
| I, K, M, O, T | yes | 993 | 0.13 | 801 | 239 | 0.05 | 239 |
| c. PAe000114 Experiment | | | | | | | |
| I | n/a | 5997 | 0.031 | 6503 | 1274 | 0.072 | 1193 |
| K | n/a | 2829 | 0.066 | 2586 | 915 | 0.066 | 858 |
| M | n/a | 4277 | 0.043 | 4381 | 1251 | 0.059 | 1211 |
| O | n/a | 4713 | 0.048 | 4752 | 1122 | 0.072 | 1015 |
| T | n/a | 3217 | 0.028 | 3513 | 1179 | 0.067 | 1125 |
| I, K, M, O, T | no | 5987 | 0.0281 | 6674 | 1356 | 0.05 | 1347 |
| I, K, M, O, T | yes | 6711 | 0.0355 | 7261 | 1326 | 0.04 | 1426 |
| K, M, O, T | no | 4765 | 0.0293 | 5223 | 1258 | 0.06 | 1197 |
| K, M, O, T | yes | 5685 | 0.0384 | 5973 | 1334 | 0.067 | 1290 |
| d. iPRG2008 Experiment | | | | | | | |
| I | n/a | 148 | 0.056 | 145 | 43 | 0.045 | 50 |
| K | n/a | 673 | 0.029 | 708 | 255 | 0.047 | 258 |
| M | n/a | 555 | 0.053 | 547 | 191 | 0.032 | 197 |
| O | n/a | 497 | 0.023 | 576 | 182 | 0.046 | 182 |
| T | n/a | 408 | 0.054 | 402 | 164 | 0.048 | 168 |
| I, K, M, O, T | no | 725 | 0.0438 | 727 | 228 | 0.064 | 221 |
| I, K, M, O, T | yes | 878 | 0.0367 | 913 | 316 | 0.059 | 308 |
| K, M, T | no | 712 | 0.0501 | 708 | 235 | 0.044 | 235 |
| K, M, T | yes | 892 | 0.0647 | 877 | 298 | 0.069 | 289 |
| e. iPRG2008-NE Experiment | | | | | | | |
| K | n/a | 241 | 0.027 | 216 | 154 | 0.052 | 152 |
| M | n/a | 357 | 0.074 | 387 | 106 | 0.019 | 122 |
| T | n/a | 85 | 0.044 | 91 | 49 | 0.041 | 50 |
| K, M, T | no | 341 | 0.0629 | 335 | 149 | 0.04 | 153 |
| K, M, T | yes | 805 | 0.0961 | 708 | 239 | 0.025 | 249 |
| f. SKHep-HLA-I Experiment | | | | | | | |
| K | n/a | 36 | 0.049 | 41 | n/a | n/a | n/a |
| M | n/a | 25 | 0.2 | 3 | n/a | n/a | n/a |
| O | n/a | 6 | 0.2 | 5 | n/a | n/a | n/a |
| T | n/a | 14 | 0.12 | 9 | n/a | n/a | n/a |
| K, M, O, T | no | 56 | 0.14 | 3 | n/a | n/a | n/a |
| K, M, O, T | yes | 180 | 0.054 | 180 | n/a | n/a | n/a |

Table 2 (below): Comparison between modeling results using a single engine or a combination of several engines in stages (using matching information), based on data generated by a unique fragmentation mechanism or through multiple mechanisms, incorporating in stages one, none or several additional sources of information to the process of meta-scoring. The indices used are the same as in Table 1, to which P (PHENYX) is added. Process performance is reported as the number of spectrum-sequence allocations recovered in overcoming a particular error rate measured as DHR (0.01, 0.05 and 0.1). For additional information sources, 'ALL' indicates that all sources of information described that were available on that data were incorporated; 'NONE' indicates that no additional sources of information were used.

TABLE 2

| Engine (%) | frag. mech. | Additional Information sources | No. retrieved spectra | | |
|---|---|---|---|---|---|
| | | | DHR <= 0.01 | DHR <= 0.05 | DHR <= 0.1 |
| a. Serum frac. RP pH basic Experiment | | | | | |
| M | CID | NONE | 393 | 524 | 619 |
| M | CID | error m/z precursor | 444 | 569 | 671 |
| M | CID | error retention time | 418 | 548 | 657 |
| M | CID | error retention time fractioning | 453 | 576 | 656 |
| M | CID | forms alt. -electric charge | 424 | 638 | 744 |
| M | CID | Internal targets | 420 | 552 | 647 |
| M | CID | Delta punctuation | 401 | 525 | 622 |
| M | CID | Precursor protein -experiment | 660 | 798 | 915 |
| M | CID | ALL | 832 | 948 | 1028 |
| b. Ecoli SILE-SILAC Experiment | | | | | |
| M | CID | NONE | 5687 | 7424 | 8302 |
| M | CID | alt. forms - isotopic signatures | 6458 | 7724 | 8618 |
| M | CID | Precursor protein -experiment | 6458 | 8122 | 9125 |
| M | CID | precursor protein fraction | 6084 | 7539 | 8661 |
| M | CID | ALL | 7750 | 8911 | 9637 |

TABLE 2-continued

| Engine (%) | frag. mech. | Additional Information sources | No. retrieved spectra DHR <= 0.01 | DHR <= 0.05 | DHR <= 0.1 |
|---|---|---|---|---|---|
| c. HLA CID-ETD Experiment | | | | | |
| M | CID, ETD | NONE | 4 | 4 | 4 |
| M | CID, ETD | alt. forms - fragmentation mechanisms | 169 | 195 | 229 |
| K | CID, ETD | NONE | 1 | 1 | 1 |
| K | CID, ETD | alt. forms - fragmentation mechanisms | 128 | 215 | 232 |
| T | CID, ETD | NONE | 3 | 3 | 3 |
| T | CID, ETD | alt. forms - fragmentation mechanisms | 43 | 64 | 76 |
| M, K | CID, ETD | alt. forms - fragmentation mechanisms | 211 | 322 | 397 |
| M, K, T | CID, ETD | alt. forms - fragmentation mechanisms | 256 | 336 | 421 |
| d. Fosfopeptides ABRF2010 Experiment | | | | | |
| I | CID | NONE | 3 | 3 | 3 |
| I | CID | internal targets | 4 | 4 | 4 |
| I | CID | alt. forms - electric charge | 6 | 6 | 6 |
| I | CID | m/z precursor error | 9 | 9 | 9 |
| I | CID | specific extremes | 11 | 11 | 11 |
| I | CID | supplementary scores | 18 | 18 | 18 |
| I | CID | Precursor protein -experiment | 15 | 15 | 15 |
| I | CID | ALL | 20 | 20 | 21 |
| K | CID, ETD | NONE | 8 | 8 | 8 |
| K | CID, ETD | alt. forms - fragmentation mechanisms | 26 | 26 | 30 |
| O | CID, ETD | NONE | 2 | 2 | 2 |
| O | CID, ETD | alt. forms - fragmentation mechanisms | 21 | 21 | 25 |
| M | CID, ETD | NONE | 13 | 13 | 13 |
| M | CID, ETD | alt. forms - fragmentation mechanisms | 26 | 26 | 28 |
| T | CID, ETD | NONE | 10 | 10 | 10 |
| T | CID, ETD | alt. forms - fragmentation mechanisms | 15 | 15 | 15 |
| P | CID, ETD | NONE | 13 | 13 | 13 |
| P | CID, ETD | alt. forms - fragmentation mechanisms | 26 | 26 | 29 |
| M, P | CID, ETD | alt. forms - fragmentation mechanisms | 35 | 35 | 36 |
| M, K | CID, ETD | alt. forms - fragmentation mechanisms | 31 | 31 | 34 |
| M, O | CID, ETD | alt. forms - fragmentation mechanisms | 27 | 27 | 36 |
| M, T | CID, ETD | alt. forms - fragmentation mechanisms | 22 | 23 | 23 |
| K, T | CID, ETD | alt. forms - fragmentation mechanisms | 25 | 25 | 31 |
| O, T | CID, ETD | alt. forms - fragmentation mechanisms | 20 | 20 | 22 |
| O, P | CID, ETD | alt. forms - fragmentation mechanisms | 26 | 26 | 34 |
| K, P | CID, ETD | alt. forms - fragmentation mechanisms | 32 | 32 | 42 |
| K, O | CID, ETD | alt. forms - fragmentation mechanisms | 29 | 29 | 32 |
| P, T | CID, ETD | alt. forms - fragmentation mechanisms | 27 | 27 | 30 |
| M, I | CID, ETD | alt. forms - fragmentation mechanisms | 20 | 20 | 25 |
| K, I | CID, ETD | alt. forms - fragmentation mechanisms | 18 | 18 | 20 |
| O, I | CID, ETD | alt. forms - fragmentation mechanisms | 24 | 24 | 33 |
| P, I | CID, ETD | alt. forms - fragmentation mechanisms | 16 | 16 | 22 |
| T, I | CID, ETD | alt. forms - fragmentation mechanisms | 16 | 16 | 16 |
| O, T, I | CID, ETD | alt. forms - fragmentation mechanisms | 20 | 24 | 24 |
| M, P, O | CID, ETD | alt. forms - fragmentation mechanisms | 35 | 35 | 36 |
| M, P, I | CID, ETD | alt. forms - fragmentation mechanisms | 21 | 21 | 25 |

What is claimed is:

1. A method for identifying peptides and proteins from mass spectrometry data and sequence database searching, using at least two different search engines, in which models of distribution of spectrum-peptide allocation scores for peptide candidates allocated by each of said search engines are obtained and a probability value or an error rate from these models is assigned to each spectrum-peptide allocation score, comprising:
  (a) modelling through generalized Lambda distribution (GLD) functions the spectrum-peptide allocation scores for peptide candidates calculated by each search engine, and calculating the probability values of spectrum-peptide allocation;
  (b) calculating the degree of overlap of peptide candidate results between the search engines used, using matching parameters of peptide sequence identifications, wherein those matching parameters are defined as the number of search engines that provide the same candidate peptide provided by other search engines;
  (c) building spectrum-peptide allocation meta-scores (S) from spectrum-peptide allocation probability values calculated in step (a) and matching parameters used in step (b) for the group of all search engines used, wherein the meta-score (S) for a spectrum j is built using the equation:

$$S_j = \underset{k}{\mathrm{argmax}}(GLD(1 - p_{jk}, 0, 0.2142, 0.1488, 0.1488) + \beta A_{jk}),$$

where $p_{jk}$ is the p-value calculated by the GLD model for a given k search engine associated with a candidate peptide, $\beta$ is a coefficient whose value is optimized for the mass spectrometry data, $A_{jk}$ is the matching parameter that indicates the number of other search engines that have provided the same candidate peptide as the kth engine for the jth spectrum and $$\underset{k}{\mathrm{argmax}}$$

is the value of the search engine k that maximizes the sum of 1.) the percentile function value of the GLD in the p-value $p_{jk}$ (GLD(1−$p_{jk}$, 0, 0.2142, 0.1488, 0.1488)) and 2.) $\beta A_{jk}$; and (d) modelling meta-scores (S) built in step (c) using generalized Lambda distribution (GLD) functions, obtaining probability values of spectrum-peptide allocation, error rates or any other measures by which to obtain a statistical classification of peptide sequence allocation, for the group of all search engines used.

2. The method of claim 1, characterized in that step (d) is optional if the sequence databases used are hybrid target or decoy databases.

3. The method of claim 1, characterized in that the error rate used is given by a false discovery rate (FDR).

4. The method of claim 1, characterized in that the error rate used is determined by a decoy hit rate (DHR), by a probability of obtaining at least one false positive (FWER) or by any other statistical quantities that give a measure of precision error in the allocations obtained.

5. The method of claim 1, characterized in that a different weight coefficient is assigned to each search engine during the meta-scoring phase, being this set a priori or calculated on the basis of any characteristic of the search engine or the sequence databases used, for which the results of some search engines over others can be favoured.

6. The method of claim 1, characterized in that a relationship is established between the meta-score calculated for a spectrum-peptide allocation and the characteristics of the sequence of the peptide candidate, such as length, presence or absence of subsequences or structural motifs as well as the matching of the sequence of the peptide with what is expected from the cutting mechanism of the chemical agent used in the digestion of proteins.

7. The method of claim 1, characterized in that a relationship is established between the meta-score calculated for a peptide spectrum allocation and other measurable variables, such as the error observed in measuring the mass of the precursor, ion mobility, the prediction of retention time during chromatographic separation, the prediction of the isoelectric point in a possible separation by isoelectric focusing, or similar measures obtained from variants of these techniques, or transformation of said measures.

8. The method of claim 7, characterized in that for each spectrum, the best scores from each of the search engines are obtained, said scores are subjected to meta-scoring, using at least one additional sources of information selected from the group consisting of:
  related to the physicochemical characteristics of the candidate peptide sequences, such as the error of the mass/charge ratio value (m/z) in the precursor ion, the time retention error or the fragmentation retention time error;
  related to the expected behaviour of the chemical agent or enzyme that has generated the peptides analyzed by mass spectrometry, such as the number of internal targets or the number of specific extremes;
  related to the generation of multiple spectra from the same peptide, such as alternative forms of electric charge, the isotopic signatures, chemical modifications or fragmentation mechanisms;
  related to specific search engine characteristics and their performance depending on the type of data, such as the electric charge of the precursor ion, the fragmentation mechanism, delta scores or additional scores;
  related to the precursor protein of the candidate peptides, such as the precursor protein in a complete experiment, the precursor protein in a fraction of an experiment or the precursor protein by clustering; and
  each search engine meta-scores are rearranged, taking the best meta-score of each search engine to complete the meta-scoring phase.

9. The method of claim 8, characterized in that numerical transformations of the additional sources of information are used, whether they be transformations of order, or nonlinear transformations of probability densities calculated from these additional sources of information, either by replacing them or in combination with them, using these transformations as sources of additional information.

10. The method of claim 1, characterized in that extended matching parameters, defined as the number of other search engines that provide, as best candidate, the same peptide that one of the given candidates provided by a search engine, are used.

11. The method of claim 1, characterized in that the matching parameter is defined in its weighted form using weight coefficients.

12. The method of claim 1, characterized in that different searches conducted on the same collection of spectra using different combinations of configurable parameters of the same search engine are treated as searches conducted by different search engines.

13. The method of claim 1, wherein the method establishes a relationship between the meta-score calculated for a spectrum-peptide allocation and structural information of a tandem mass spectrometry (MS/MS) spectrum obtained by de novo interpretation.

14. The method of claim 8, characterized in that additional sources of information for each search engine are integrated in stages in the process of meta-scoring, generating meta-scores from each search engine and establishing an order of integration of said additional sources of information, so that for a given search engine a single additional source of information to the meta-score is incorporated, ignoring the matching information with other search engines, and a new meta-scoring is obtained, repeating this process until that all additional sources of information have been incorporated into the meta-score and later adding the matching information.

15. The method of claim 1, wherein the search engines are integrated in stages in the process of meta-scoring, establishing an order of integration of the various search engines, starting with the integration of two search engines, and treating the meta-score in this process as a new consensus engine, later taking this result and integrating it with a third search engine, repeating the process successively until all the search engines used in the process have been incorporated into the "consensus".

16. A non-transitory computer-readable medium configured to store logic executable by a device for analysis of results of tandem mass spectrometry, said device configured for the identification of peptides and proteins, wherein the device implements the method of claim 1.

17. The method of claim 15, characterized in that a different weight coefficient is assigned to each search engine during the meta-scoring phase, being this set a priori or calculated on the basis of any characteristic of the search engine or the sequence databases used, for which the results of some search engines over others can be favoured.

* * * * *